(12) United States Patent
Lall et al.

(10) Patent No.: US 11,850,092 B2
(45) Date of Patent: Dec. 26, 2023

(54) DUAL MODALITY ENDOCAVITY BIOPSY IMAGING SYSTEM AND METHOD

(71) Applicant: Hybridyne Imaging Technologies, Inc., Toronto (CA)

(72) Inventors: Terrence Lall, Toronto (CA); James A. Ionson, Lexington, MA (US)

( * ) Notice: Subject to any disclaimer, the term of this patent is extended or adjusted under 35 U.S.C. 154(b) by 0 days.

(21) Appl. No.: 17/496,854

(22) Filed: Oct. 8, 2021

(65) Prior Publication Data

US 2022/0273265 A1 Sep. 1, 2022

Related U.S. Application Data

(63) Continuation of application No. 16/378,901, filed on Apr. 9, 2019, now abandoned, which is a continuation of application No. 15/990,993, filed on May 29, 2018, now abandoned, which is a continuation of application No. 14/605,144, filed on Jan. 26, 2015, (Continued)

(51) Int. Cl.
| | |
|---|---|
| *A61B 8/00* | (2006.01) |
| *A61B 8/08* | (2006.01) |
| *A61B 8/12* | (2006.01) |
| *A61B 6/12* | (2006.01) |
| *A61B 6/00* | (2006.01) |
| *A61B 10/02* | (2006.01) |
| *A61N 5/10* | (2006.01) |
| *A61B 6/03* | (2006.01) |

(52) U.S. Cl.
CPC ............ *A61B 8/4416* (2013.01); *A61B 6/037* (2013.01); *A61B 6/12* (2013.01); *A61B 6/481* (2013.01); *A61B 6/5247* (2013.01); *A61B 8/0841* (2013.01); *A61B 8/12* (2013.01); *A61B 8/5207* (2013.01); *A61B 10/0233* (2013.01); *A61N 5/1001* (2013.01); *A61N 5/1027* (2013.01); *A61B 6/482* (2013.01); *A61B 6/5235* (2013.01); *A61B 8/465* (2013.01); *A61N 5/1049* (2013.01); *A61N 5/1071* (2013.01)

(58) Field of Classification Search
CPC ....... A61B 8/12; A61B 8/4416; A61B 8/5207; A61B 6/037; A61B 6/5247; A61B 6/482; A61B 6/5235

See application file for complete search history.

(56) References Cited

U.S. PATENT DOCUMENTS

| | | |
|---|---|---|
| 6,443,902 B1 | 9/2002 | Sasady |
| 7,373,197 B2 | 5/2008 | Daighighian et al. |

(Continued)

*Primary Examiner* — Jason M Ip
(74) *Attorney, Agent, or Firm* — Fox Rothschild LLP

(57) ABSTRACT

A dual modality endocavity imaging and treatment system for detection of cancer and targeted biopsy and treatment procedures, comprising: a housing; a nuclear detector system housed within the housing and configured for detecting nuclear radiation imaging data; an ultrasound detector system housed within the housing for detecting ultrasound imaging data; a needle associated with the housing and adjustably positionable relative thereto; and a data processing module configured to receive the nuclear radiation imaging data and the ultrasound imaging data and to generate and output an image showing the relative position of the needle and an endocavity object of interest. The needle may include a distinct radiation signature to facilitate imaging thereof.

12 Claims, 7 Drawing Sheets

Related U.S. Application Data now abandoned, which is a continuation-in-part of application No. 14/163,183, filed on Jan. 24, 2014, now abandoned, which is a continuation-in-part of application No. PCT/US2013/033473, filed on Mar. 22, 2013.

(60) Provisional application No. 61/614,171, filed on Mar. 22, 2012.

(56) References Cited

U.S. PATENT DOCUMENTS

| | | | |
|---|---|---|---|
| 7,652,259 B2 * | 1/2010 | Kimchy | A61B 6/4417 600/407 |
| 8,825,135 B2 * | 9/2014 | Okada | A61B 6/547 600/407 |
| 2004/0204646 A1 * | 10/2004 | Nagler | A61B 1/05 600/436 |
| 2007/0055128 A1 * | 3/2007 | Glossop | A61B 1/018 600/407 |

* cited by examiner

DUAL MODALITY ENDOCAVITY BIOPSY IMAGING SYSTEM AND METHOD

CROSS-REFERENCE TO RELATED APPLICATIONS

This is a continuation application of U.S. application Ser. No. 16/378,901, filed 9 Apr. 2019, which is a continuation application of U.S. application Ser. No. 15/990,993 filed 29 May 2018, which is a continuation application of U.S. application Ser. No. 14/605,144, filed 26 Jan. 2015, which is a continuation-in-part of U.S. application Ser. No. 14/163,183, filed 24 Jan. 2014, which is a continuation-in-part of PCT Application No. PCT/US2013/033473, filed 22 Mar. 2013, which claims the benefit of U.S. Provisional Application No. 61/614,171, filed 22 Mar. 2012, each of which are incorporated herein by reference.

STATEMENT OF GOVERNMENT RIGHTS

The present invention was made with government support under contract number DE-AC02-98CH10886 awarded by the U.S. Department of Energy. The United States government may have certain rights in this invention.

BACKGROUND

I. Field of the Invention

This invention relates to the field of radiation imaging, targeted biopsies and treatment of cancer. In particular, the invention relates to a novel dual modality probe that has an integrated solid-state semiconductor detector, ultrasound device and a method of using such probe to enable targeted biopsies and treatment of disease(s).

II. Background of the Related Art

In medical imaging applications, two technologies are generally used: ultrasound and nuclear medical imaging. The benefits of the ultrasound technology are that it enables a very compact design of a probe and is powerful in revealing the anatomical structures of the organs. However, the ultrasound technology is not an ideal tool in cancer detection and diagnosis because the ultrasound technology can only generate anatomical images, whereas functional images are needed, especially in diagnosis of cancer(s) at the early stage. For example, in prostate cancer diagnosis, the ultrasound probe produces and subsequently records high-frequency sound waves that bounce off the prostate and reflect the density variations within the prostate. The probe transforms the recorded sound waves into video- or photographic-images of the prostate gland. The probe generates images at different angles to help the physician estimate the size of the prostate and detect abnormal growths with a density different than the surrounding tissue; however, benign and cancerous tumors cannot easily be distinguished by ultrasound. In addition, if the patient had radiation treatment in or around the prostate before, the fibrous tissues can be mistakenly identified as tumors during the interpretation of the sonograms. Hence, while the ultrasound probes can be designed to be very compact and easy to carry, handle and operate, their inability to distinguish benign and cancerous tumors makes them unsuitable for functional imaging required in cancer imaging, diagnosis and image-guided treatment.

By contrast, the traditional diagnostic nuclear medical imaging techniques have the capacity to provide the desirable functional images. Such methods use radioactive tracers, short-lived isotopes, which emit gamma rays from within the body and are linked to chemical compounds, permitting the characterization of specific physiological processes. The isotopes can be given by injection, inhalation, or by mouth. Normally an imaging device (e.g., Anger gamma camera as described in U.S. Pat. No. 3,011,057, which is incorporated herein by reference) is used to image single photons emitted from an organ. The camera builds up an image of the points where radiation is emitted. This image is then enhanced by a computer, projected on a monitor, and viewed by a physician for indications of cancer. Exemplary commercial nuclear imaging systems that are capable of producing functional images include PET (Positron Emission Tomography) and SPECT (Single Photon Emission Computerized Tomography). Some of these systems are based on scintillator detectors, such as NaI, CsI and BGO, plus photon-sensing devices, such as photomultipliers or photodiodes (see, e.g., U.S. Pat. No. 5,732,704, incorporated herein by reference). Other systems are based on high-purity germanium (HPGe) crystals. Although HPGe itself is small, it needs a complex cooling system to work at cryogenic temperatures (e.g., −180° C.). Hence, all of these systems, either based on scintillator detectors or HPGe crystals, are bulky and can only be integrated into an external detection system. However, since the detectors of such external systems are located far away from the imaged organs, they have a poor detection efficiency and low spatial resolution, which limit such detector's ability to pinpoint the exact positions of cancerous tissues in a small organ. All these drawbacks limit the usefulness of such radiation detection systems in diagnosing cancer in small organs, e.g. prostate glands, particularly for small tumors.

In view of the foregoing problems and drawbacks encountered in the conventional diagnostic techniques, a compact endocavity diagnostic probe was developed for nuclear radiation detection shown in FIG. 1A and disclosed in the U.S. patent application Ser. No. 13/077,627 filed on Mar. 31, 2011. Although this probe can generate images with high spatial resolution, it has a limited field-of-view (FOV), which was addressed by an improved diagnostic probe illustrated in FIG. 1B and disclosed in the U.S. Provisional Patent Application No. 61/495,695 filed on Jun. 10, 2011. The probe was further improved by incorporating an interwoven collimator to afford 3D imaging, which is disclosed in the PCT Patent Application No. PCT/US2010/029409 filed on Oct. 21, 2010. Each of the aforementioned U.S. and PCT Patent Applications is incorporated by reference in its entirety as if fully set forth in this specification.

However, the described compact endocavity probes have been primarily designed for diagnosis of cancer and other abnormalities in an imaged organ. Hence, it is highly desirable to develop a dual modality probe that integrates the benefits of both radiation imaging and ultrasound imaging for the purpose of enabling targeted biopsies and treatment of diseases, including cancer.

SUMMARY

In view of the above-described needs and goals, the inventors have devised embodiments of the present invention in which methods for treating disease(s), including cancer, using a compact endocavity probe are provided. In its most general form, the methods involve (1) monitoring the physical or functional changes in the abnormal tissue(s)

using the probe during the course of treatment; (2) optimizing the activity of radiopharmaceuticals during the nuclear medicine therapy; (3) guiding the implantation of the isotope impregnated capsules and their locations during radiotherapy; and (4) guiding the use of cryo-surgery, high-intensity focused ultrasound or other ablation techniques for image-guided treatment of cancerous tissues.

In the first embodiment, the method of treating diseases involves using the probe to identify suspected abnormal tissues and enable targeted biopsies to verify disease within the tissue. The probe is then used to deliver targeted treatment to the diseased tissue and monitor the physical or functional changes of the abnormal tissues and their response to treatments. This procedure is similar to the imaging procedure during the diagnosis process, but it is done during or after the treatment of the disease. The acquired images during the treatment (often at different times) can be compared with each other or to the images obtained during the diagnosis process. The results can help practitioners determine the effectiveness of different treatment procedures, or the changes in the tumor volume and uptake of a diagnostic radiotracer as part of an active surveillance program.

In the second embodiment, the method of treating diseases involves optimizing the activity of radiopharmaceuticals during the nuclear medicine therapy. Because the radiopharmaceutical used for nuclear medicine therapy emits radiation similar to the tracer used for the diagnosis process, it can also be imaged in the same way by the probe. This imaging process can help physicians monitor the metabolism, uptake or binding of the drug with the target tissue. It can also be used to understand the wash-out kinetics of the drugs. In this case, the radiopharmaceutical can be administrated orally, by IV injection, or by other known means.

In the third embodiment, the probe can be used to assist the radiotherapy process. The radiotherapy refers to implanting capsules of isotopes to sites of cancer tissues, e.g. brachytherapy. During the procedure, the probe can be used to monitor the position of the capsules and make sure the seeds are placed at the right positions to optimally irradiate the diseased tissue, while minimizing the damage to the nearby healthy tissue. In a similar manner, the probe can image any changes in the positions of the radioactive seeds with respect to the cancerous tissues over time. The procedure may advantageously utilize co-registration of probe images with other anatomical images generated by other modalities. A second modality, e.g. CT, MRI, Ultrasound, etc. can be a separate system or it can be integrated into the probe, e.g. a bi-modality imaging with both SPECT and an ultrasound transducer. Alternatively, the procedure can also be performed without the assistance of other imaging modalities. In this case, multiple energy windows of the probe can be used because different isotopes generate different gamma-ray energy lines. For example, if radiotherapy uses one isotope (energy 1), and a radiopharmaceutical diagnostic tracer for imaging cancer tissues uses another isotope (energy 2), it is possible to take images of these two isotopes at different energy windows (window 1 for energy 1 and window 2 for energy 2). By co-registering these images, a practitioner can decide where the therapy seed should be delivered to best treat the cancerous tissues, and one distinguish disease from vessels and inflammation. Alternatively, the procedure can also be done utilizing only one energy window as long as the energy window is wide enough to cover the energy signatures, i.e., lines from both radiotherapy isotope and radiopharmaceutical tracer. While, as discussed above, the procedure can be done using two or more radioisotopes, the procedure can also be done using the same isotope for imaging both the cancerous tissues and the radiotherapy seeds in one energy window. Specifically, the tissues and the seed(s) are shown in one image as different hot areas. Their relative positions indicate how close the seeds are to the cancerous tissues. Merging of the hot areas will tell the practitioner that the seed(s) reaches the target site. Similarly, the cold spots can accurately localize those regions that are receiving radiation below a desired threshold level for optimal brachytherapy treatment.

These and other characteristics of the methods for treating diseases using the gamma-ray sensitive endocavity probe will become more apparent from the following description and illustrative embodiments which are described in detail with reference to the accompanying drawings. Similar elements in each figure are designated by like reference numbers and, hence, subsequent detailed descriptions thereof may be omitted for brevity.

DETAILED DESCRIPTION OF THE INVENTION

The present invention is directed to methods of treating diseases, such as cancer, by employing a radiation imaging probe disclosed in U.S. Patent Publication No.: US 2011-0286576 A1 filed on Mar. 31, 2011 and U.S. Provisional Pat. App. No. 61/495,695 filed on Jun. 10, 2011, published as PCT Publication No.: WO 2012-171009 A1, that offers a compact size, yet provides a high energy resolution, high spatial resolution, and a high detection efficiency. Each of the aforementioned U.S. Patent Applications is incorporated by reference in its entirety as if fully set forth in this specification. The probe preferably has an array of semiconductor-based detectors, a collimator, signal processing circuits, ultrasound components, biopsy and treatment needle. The semiconductor-based detectors are preferably made from elements of groups III and V, groups II and VI and group IV of the periodic table, such as, but are not limited to, CdZnTe (Cadmium Zinc Telluride), CdTe (Cadmium Telluride), CdMnTe (Cadmium Manganese Telluride), CdMgTe (Cadmium Magnesium Telluride), HgI$_2$ (Mercuric Iodide), or TlBr (Thallium Bromide). The collimator may have parallel apertures, fan-beam pattern of apertures, focused-beam pattern of apertures or interleaved apertures described in PCT Patent Application No. PCT/US2010/029409, which is incorporated herein by reference in its entirety. The ultrasound components are standard, compact components that are integrated into the radiation probe and the biopsy/treatment needle is dual purpose, capable of extracting targeted biopsy tissue as well as delivering treatment medication to the diseased tissue. The biopsy/treatment needle can be imaged by the ultrasound component of the probe during biopsy and imaged by both the radiation detector and ultrasound components during treatment since the treatment medication will also have a radiation signature.

In accordance with the present disclosure, in one embodiment the method comprises monitoring the physical or functional changes in the abnormal tissue during administration of chemotherapeutics, immunotherapeutics and other procedures, such as ionizing radiation and localized freezing or heating, that may retard or improve the course of the disease progression during the course of treatment. In another embodiment, the method comprises monitoring and optimizing therapeutic drug administration. In yet another embodiment, the method comprises guiding the implantation of the isotope impregnated capsules during radiotherapy by using either a multi-modality imaging or a single-modality imaging. In the single modality embodiment, the imaging is provided via co-registration of multiple energy windows or via registration in one sufficiently wide energy window.

Figure 2A:
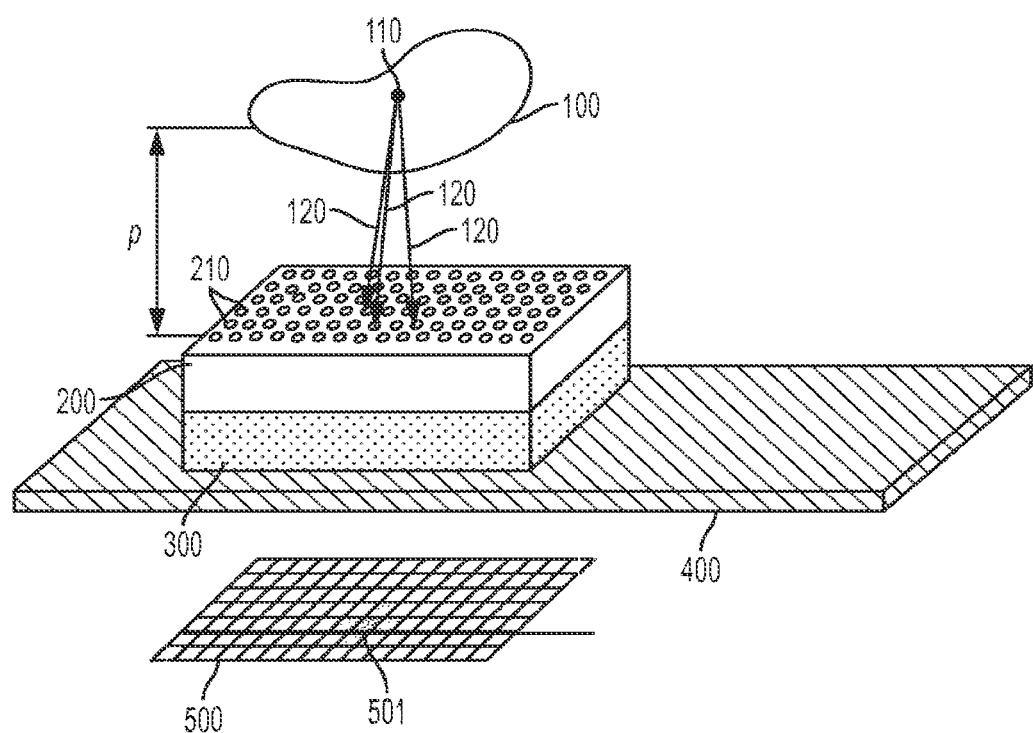
FIG. 2A illustrates the principle of operation of a CdZnTe (CZT) based gamma endocavity diagnostic probe.
Figure 2B:
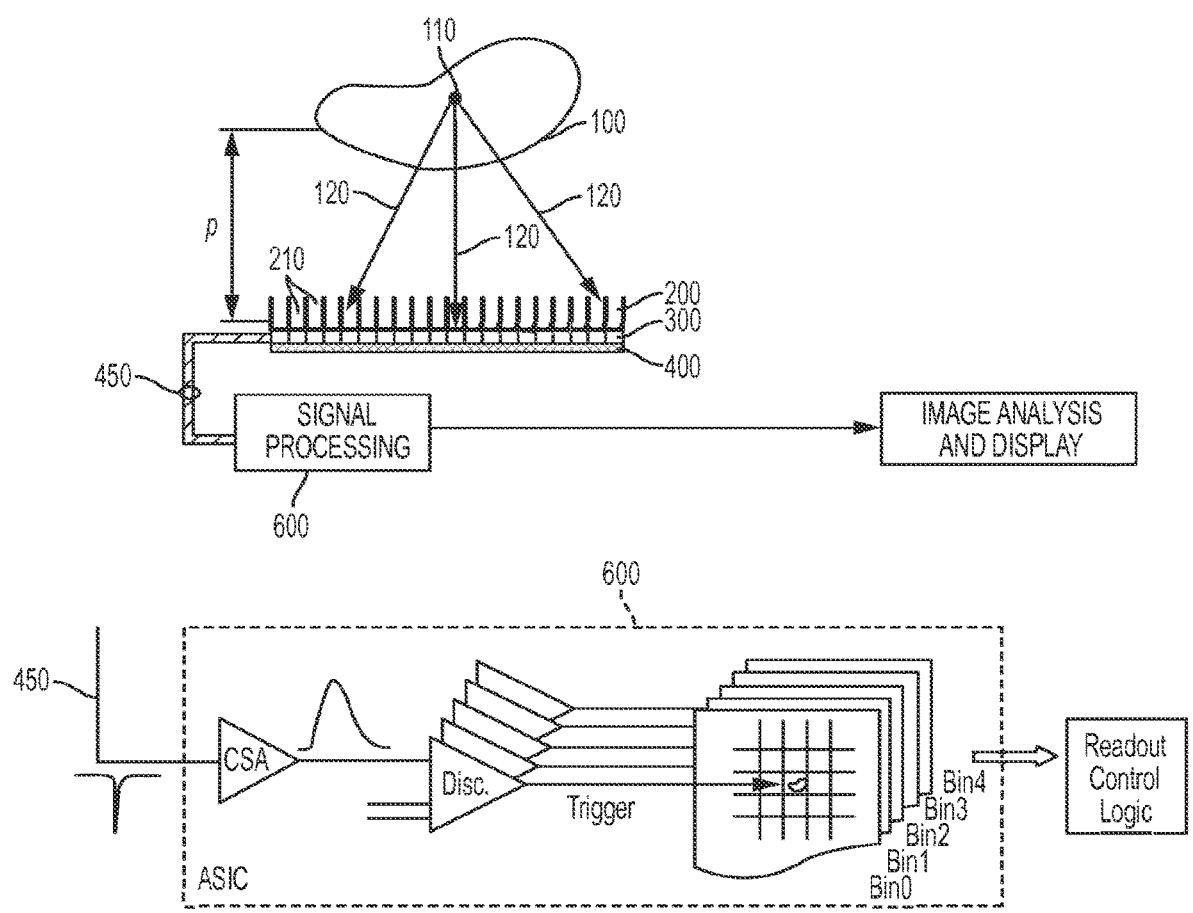
FIG. 2B is a schematic drawing showing a signal processing chain for the endocavity diagnostic probe.

FIG. 2A illustrates how the probe generally works, assuming an object of interest or a hot spot 110 (e.g. cancerous tissue) is inside the imaged organ 100. The imaged organ 100 is preferably a prostate gland. When radiopharmaceuticals are administered into patient's body, the radioactive tracer will concentrate more in the hot spot 110 than in the surrounding healthy tissue. Typically, the radioactive isotope within the tracer is $^{67}$Ga, $^{123}$I, $^{125}$I, $^{131}$I, $^{111}$In, $^{81}$Kr, $^{99m}$Tc, $^{75}$Se, $^{201}$Tl, $^{133}$Xe, or $^{103}$Pd. This isotope will decay and emit gamma-ray photons with a specific energy, e.g. 140-keV gamma rays for Tc-99m-containing radiotracers, in all directions. Only the photons 120 with trajectories parallel to the axis of the holes 210 of the collimator 200 can reach the detector 300. Most of these photons will ionize the detector 300 and generate electron-hole pairs that are separated and guided to the contacts by the internal electric field. The number of electron-hole pairs generated by a photon is proportional to the photon's energy. Because the detector 300 is typically negatively biased, the electrons will drift to the anodes (pixels), while the holes will drift to the cathode. Movement of the electrons and holes under the influence of the electric field induces a current signal on the electrodes. The amplitude of this signal is proportional to the energy of the gamma-ray photon, and can be processed and read out by the front-end electronics and the control logic preferably located on the PCB board 400. As illustrated in FIG. 2B, the front-end electronics counts the photon absorption events within each voxel of the detector 300. With the guidance of the collimator 200, the region right underneath the hot spot 110 has the highest radiation counts on the readout map 500 as shown by the readout pixel 501. The accumulation of tracers in the hot spot 110 results in projection of an energy spike on the plane 500 parallel to the detector surface.

The following description of the preferred embodiments and various examples of the method for treating diseases are described. It is to be understood, however, that those skilled in the art may develop other structural and functional modifications without significantly departing from the scope of the instant disclosure.

I. Monitoring the Responsiveness to Treatment

The method comprises acquiring images during treatment, preferably at different times, from an object or objects (tissues) of interest using the endocavity probe sensitive to radiation, e.g. either x-rays or gamma-rays. Examples of suitable objects (tissues) for monitoring purposes may include, but are not limited to, a prostate gland, thyroid, breast, lymph nodes, brain, intestine, colon, heart, lungs, liver, kidneys, skeleton, gallbladder, adrenal gland, blood, etc., although the prostate gland is the preferred object for monitoring purposes. The patient is treated with a predefined therapy regimen for a selected period of time that may be any convenient period, ranging from minutes, hours to months or years. The selected monitoring and treatment time by the practitioner is determined based upon the response of the patient to the regimen acquired through the described process.

Figure 1A:
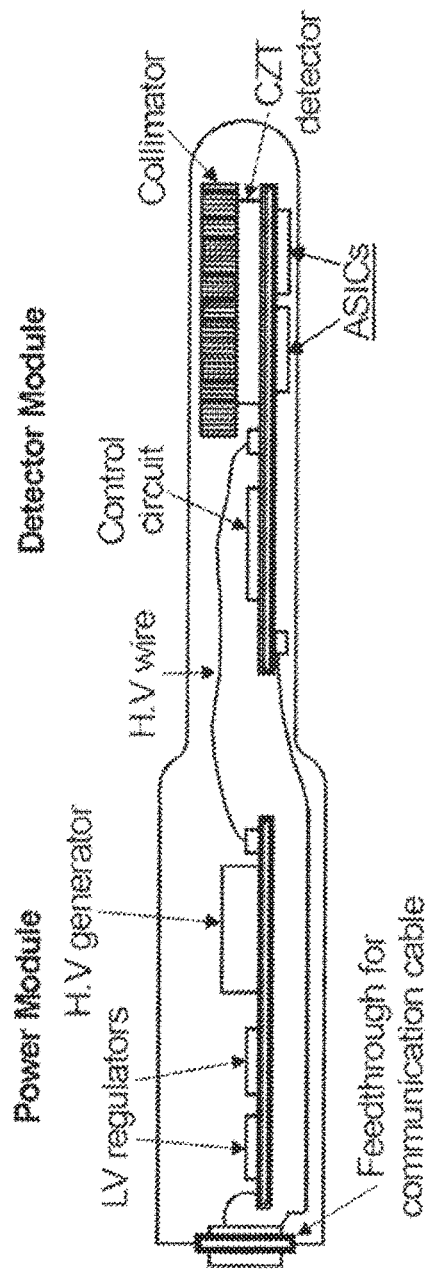
FIG. 1A illustrates an exemplary embodiment of the endocavity diagnostic probe disclosed in U.S. Patent Publication No.: US 2011-0286576 A1 and incorporated herein by reference.
Figure 1B:
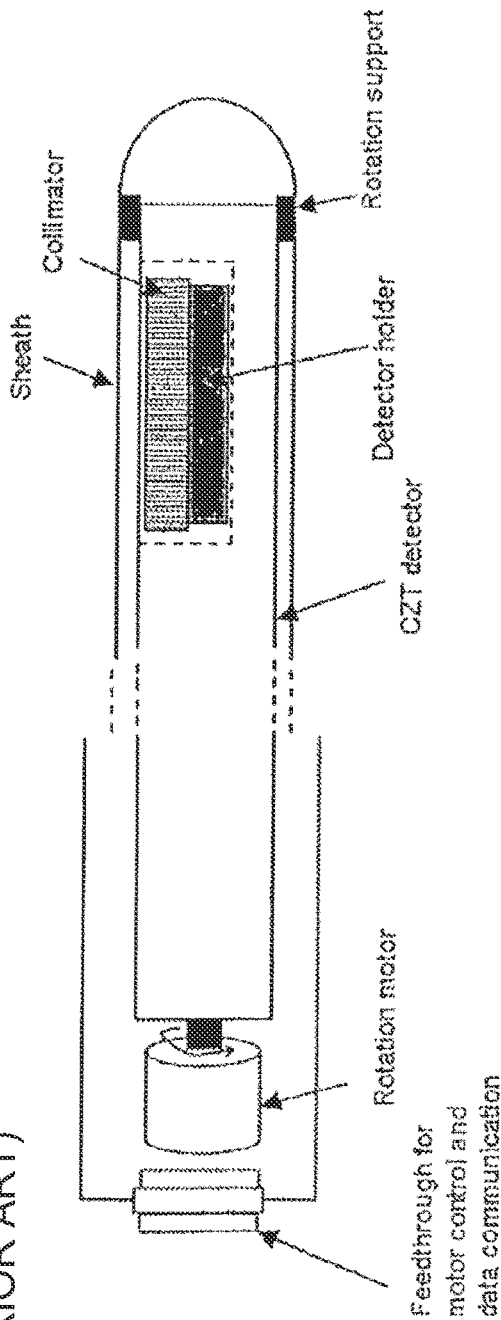
FIG. 1B illustrates an exemplary embodiment of the endocavity diagnostic probe with the enhanced FOV disclosed in PCT Publication No.: WO 2012-171009 A1 and incorporated herein by reference.

The generalized process of acquiring images during treatment includes the steps of positioning a radiation imaging probe near the object of interest; detecting the radiation emitted by the radioactive isotopes, such as $^{18}$F, $^{81m}$Kr, $^{82}$Rb, $^{67}$Ga, $^{123}$I, $^{125}$I, $^{131}$I, $^{111}$In, $^{81}$Kr, $^{99m}$Tc, $^{75}$Se, $^{201}$Tl, $^{133}$Xe, or $^{103}$Pd, in the tracers absorbed within the object as a plurality of images utilizing either stationary or rotatable probe illustrated in FIGS. 1A-1B; and processing and combining the information recorded by the detector in the plurality of images into one single image (1D, 2D or 3D) referenced to a specific time interval, e.g., 1 day, 2 days, 3 days, 4 days, etc. during a treatment or following a specific episode of a time-limited or repeated treatment. In particular, the detecting step includes collimating radiation from the object of interest; detecting collimated radiation with a semiconductor-type detector; and recording the information about the radiation detected by the semiconductor detector at a specified time point as a single image.

Preferably, a parallel-hole collimator or other fan-beam shaped collimator may be used to perform an initial scan to define the boundaries of the imaged object before an image with high spatial resolution is generated and to be used in the monitoring method. This initial scan avoids unnecessary high-resolution imaging of the areas that do not contain an object of interest. By defining the boundary conditions for imaging the full object, the start and stop positions of the scan by the probe can be specified.

Once the images are acquired at different time points during treatment, they are compared with each other or to the images obtained during the diagnosis process as part of an active surveillance to determine the effectiveness of the treatment procedure. Without being bound by theory, since the radioactive tracers will concentrate in the hot spot, e.g. diseased or cancerous tissue, inside the target organ as compared to surrounding healthy tissue, it is believed that once the subject responds positively to the treatment, the size and intensity of the hot spot will decrease primarily due to reduced localization of the radioactive tracers. In contrast, the increase in size and/or intensity of the hot spot will indicate the progression of the disease, which may require modification in treatment.

In addition to using the probe to localize hot spots to determine the effectiveness of the treatment procedure, the probe can be also used to localize the cold spots in a complementary manner, which are the tissue that experiences decrease or absence of molecular or physiological activity. For instance, the tissue can have less than normal metabolic function, scarring due to freezing/heating, radiation damage, or chemical treatment(s), or experience cellular death. These cold spots (regions) can assist in diagnosis or treatment. For example, the presence of cold spots in prostate-cancer patients receiving treatment can reveal information about the response of a diseased volume affected by brachytherapy, chemical treatment, focused ultrasound, or cryo-ablation, since the dead tissue would have a much lower uptake than either healthy or cancerous tissue. Scarred and fibrous regions may, depending on the drug, also be revealed as cold spots. Thus, by quantifying the high and low-activity regions over time, a practitioner can gain useful information about the response to different medical treatments within the gland. This approach eliminates the need for invasive procedures, such as biopsies, to follow the progress of the disease and ascertain the effect of the treatment on the target organ.

II. Optimizing Therapeutic Agent

The process generally involves monitoring changes in the metabolism, uptake or binding of the radiopharmaceutical drugs with the target tissue during therapy. It can also be used to understand the wash-out kinetics of the drugs when administrated orally, by IV injection, or by other known means.

In a preferred embodiment, the method for optimizing the administration of the therapeutic agent comprises the step of administering one or more radiolabeled therapeutic agents to a patient. If multiple radiopharmaceutical therapeutic agents, e.g. 2, 5, 10, 20, etc., are administered to the same patient, they are preferably labeled with different radioactive isotopes with the tracers and administered at different times, although labeling multiple therapeutic agents with the same radioactive isotope and administering at the same time is also envisioned. The radiopharmaceutical therapeutic agent may be administered at a therapeutic dose or at a low dose, e.g., less than 10% of a conventional therapeutic dose. The radiolabeled therapeutic agent comprises a therapeutic agent covalently or ionically bound to a radioactive isotope. Typically, the therapeutic agent is substantially non-radioactive, except for the radioactivity that is present in the isotopes of interest.

The therapeutic agent may comprise a small-molecule drug, a protein, or an antibiotic. For example the small-molecule drug may be an anti-cancer drug, a cardiac drug, a neurological drug, an anti-inflammatory agent, a non-steroidal anti-inflammatory agent, or any other agent known in the art. Examples of therapeutic agents include, but are not limited to, In111-DTPA (diethylenetriaminepenta-acetic acid), I125-fibrinogen, I131-Iodide, I131-MIBG (m-iodo-benzylguanidine), Sm153-EDTMP (Ethylenediaminotetramethylenephosphoric acid), Se75-Selenorcholesterol, and $^{131}$I (Tositumomab). Essentially any therapeutic agent may be used in the disclosed method as long as this agent is radiolabeled/tagged. While the therapeutic agents may be radiolabeled by any method known in the art, in an exemplary embodiment, the therapeutic agents are radiolabeled by chelation with radioisotopes or other tracer, such as, but are not limited to, $^{125}$I, $^{131}$I, $^{111}$In, $^{75}$Se, $^{153}$Sm, $^{201}$Tl, $^{133}$Xe, or $^{103}$Pd. This labeling process generally does not affect the pharmacological or chemical properties of the therapeutic agent, other than becoming radioactive. That is, the therapeutic agent molecule retains the same structure and biochemical properties when administered. Some exceptions may exist, such as tracers for diagnosing and treating thyroid disease, since the thyroid has a high affinity for most chemicals containing iodine, including both radioactive and non-radioactive isotopes of iodine.

The disclosed method further comprises a functional imaging step to acquire information regarding the activity of the therapeutic agent, such as: the bioactivity of the agent, the uptake of the agent, e.g., areas in the body at which the radiolabeled therapeutic agent concentrates (including desired locations and undesired locations); levels of concentration of the radiolabeled therapeutic agent; actual bioavailability of the radiolabeled therapeutic agent; kinetic information regarding the agent; and/or metabolism of the agent, of a substrate thereof, and/or an enzyme involved in the metabolism of the agent.

Based on the information obtained from the imaging step, the treatment may be modified, optimized and personalized in a subsequent treatment of the patient. In a preferred embodiment, customizing the subsequent treatment comprises determining the proper dose by setting the dose at a level that: (a) reduces a likelihood of serious adverse events and/or limits the toxicity of the subsequent administration of the therapeutic agent at the higher, therapeutic dose; and/or (b) maximizes the effectiveness of a subsequent administration of the therapeutic agent. For example, the maximum dose of the therapeutic agent is the dose that can be delivered without exceeding the maximum accumulation of the therapeutic agent in sensitive organ(s) and/or tissue(s). In contrast, the minimum dose of the therapeutic agent is the dose that is necessary to cause sufficient accumulation of the therapeutic agent at one or more desired sites in the body.

The use of this optimization method thus enables treatment to be customized for each patient, rather than relying on generic curves of bioavailability applicable to large patient populations. This method may be particularly beneficial for therapeutic agents for which it is difficult to pre-identity responders and non-responders, or to predict side effects. The information obtained during imaging may include affinity and/or location information, which is used during treatment to prevent ineffectiveness, serious adverse events, and/or toxicity of the agent.

During the imaging, the information is acquired regarding the activity of (1) the therapeutic agents, such as the bioactivity of the agent(s), the regions of high and low uptake of the agent(s), the levels of concentration of the agent(s); the actual bioavailability of the agent(s); the kinetic information regarding the agent(s); and/or the metabolisms of the agent (s), (2) the substrates, and/or (3) the enzymes involved in the metabolisms of the agents. This method thus allows a practitioner to determine whether the agent shows potentially beneficial therapeutic activity. Alternatively, if a plurality of agents is administered at the same time, it may also be possible to determine which of the plurality of potentially beneficial therapeutic agents is likely to be most effective in a particular patient. Using this strategy, the practitioner can personalize the therapeutic agent treatment for a particular patient. The method may also provide information to predict leakage or migration of therapeutic agents to surrounding healthy tissues, and risks of serious adverse events. This information may guide the practitioner to administer other therapeutic agents, such as infusion of an isotonic solution or diuretic if the therapeutic agent has a metabolism through the urinary tract, in order to quickly reduce the predicted serious adverse events.

The property of the tissue measured may include, for example, size, perfusion, a marker of viability or apoptosis, an inflammatory process, metabolism, expression of specific proteins and/or mRNA, or cancer-specific activity. For example, the radiopharmaceutical imaging agent may comprise a tracer associated with mitochondrial activity. The measured mitochondrial activity may be used to predict the effect of an antibiotic in treating bacterial infection. Alternatively, an imaging procedure may be performed in order to monitor one or more intermediary steps of the metabolism of a therapeutic drug. For example, a radiopharmaceutical agent is administered that binds to and/or is uptaken by cells that are targeted by a drug. As a result, the agent serves as a marker for metabolism of the drug, rather than of general cell activity. An example of the use of hot and cold spots generated by the endocavity probe involves drugs used to visualize primary prostate cancer, e.g., In-111-labeled ProstaScint, and blood flow, e.g., Tc-99m-labeled red blood cells. In such exemplary embodiment, it is believed that the analysis of the hot and cold spots can reveal detailed formation on the presence of tumors and the functional micro-vascular networks with red blood-cell perfusion. Thus, imaging the uptake of the tumor-imaging agent simultaneously with imaging the protrusion and outgrowth of capillary buds and sprouts from pre-existing blood vessels (or absence thereof) provides greater information on the presence or tumors within the prostate.

It is also within the scope of the present disclosure that the endocavity probe may be used instead of or in supplement to conventional imaging techniques, such as CT, external SPECT, PET or MRI. The functional information provided by the endocavity probe imaging procedures provides information not provided by such conventional imaging techniques since the detectors of such external systems are located far away from the imaged organs. As a result, these systems may have limited ability to pinpoint the exact positions of a target tissue, e.g. cancerous tissues, in small organs; although, they may provide useful information on the presence of disease, such as metastasis, in the region outside of the field of view of endocavity probe.

III. Localized Radiotherapy

Radiotherapy typically refers to implanting capsules of isotopes (also known as seeds) to sites of cancer tissues, e.g. brachytherapy, to destroy cancerous tissue. In this embodiment, a treatment needle that is physically integrated with the dual modality radiation/ultrasound imaging probe delivers the treatment capsules used in the localized radiotherapy procedure. FIGS. 3A-3C and 4A-4C illustrate an exemplary embodiment of the process for monitoring and optimizing the administration of the radioactive seeds. The process generally involves monitoring the target tissue and placing the radioactive seeds to optimally irradiate the diseased tissue, while causing the least amount of harm to the nearby healthy tissue.

Figure 3C:
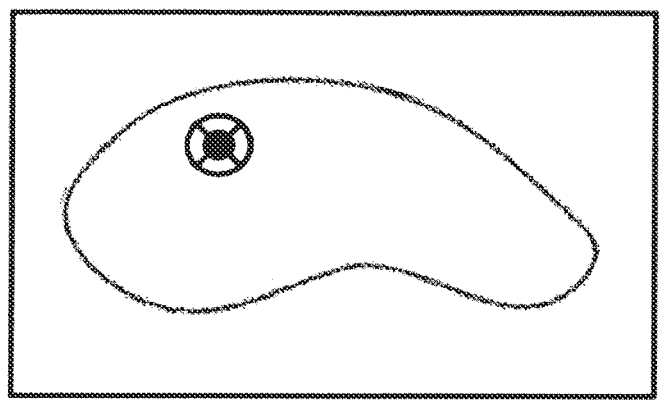
FIGS. 3A-3C are the schematic drawings showing a radiotherapy procedure with multi-modality imaging.
Figure 3B:
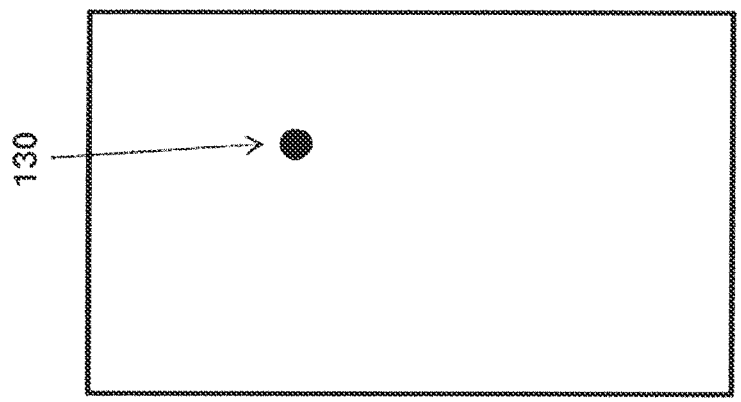
Figure 3A:
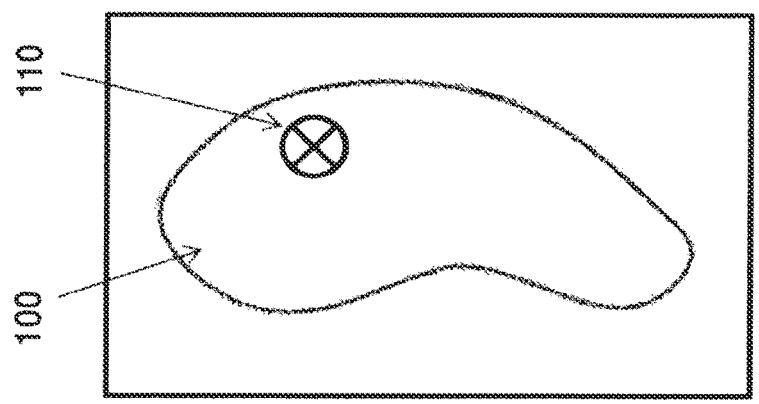
Figure 4C:
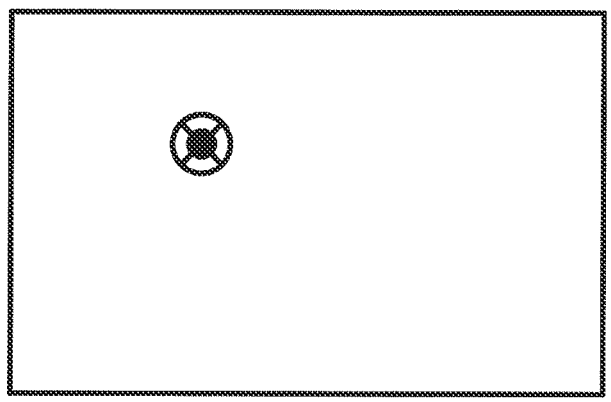
FIGS. 4A-4C are the schematic drawings showing a radiotherapy procedure with single-modality imaging using the endocavity diagnostic probe illustrated in FIGS. 1A-1B.
Figure 4B:
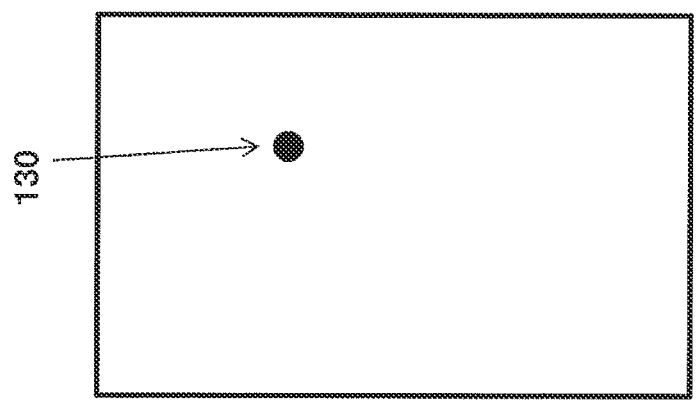
Figure 4A:
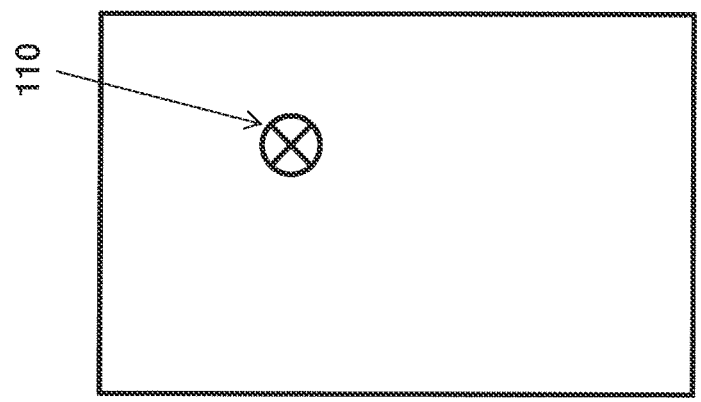

In a preferred embodiment, as illustrated in FIG. 3A, the method for localized radiotherapy comprises the step of dual modality imaging of the treated organ 100 and the target tissue 110 typically by a high-sensitivity anatomical imaging modality, e.g., CT, MRI, Ultrasound, etc. For instance, medical ultrasonography allows visualization of subcutaneous body structures including tendons, muscles, joints, vessels and internal organs for possible pathology or lesions. Typically, the frequencies used in diagnostic ultrasound are between 2 and 18 MHz. However, whatever the imaging procedure that is selected, it should generate a clinically-valuable image of an intra-body tissue 100 and the target tissue 110 that would enable prediction of the efficacy of the radiotherapy in a patient. Accordingly, in order for radiotherapy to be effective, the target tissue 110 should be sufficiently localized.

In an exemplary embodiment, prostate cancer can be imaged by utilizing dedicated transrectal ultrasound from the dual modality imaging probe. The probe is inserted into the rectum to place the transducer near the prostate. The probe then emits high-frequency sound waves and detects their return. These sound waves can then be detected and measured as they reflect off of various structures inside the body. Different types of structures reflect (or "echo") sound waves differently. These differences can be detected and an image produced showing where one type of structure stops and another begins. This procedure provides a detailed view of the area near the ultrasound probe. Measurements can be made of the size and shape of the object, its distances from the probe, and its possible makeup. For instance, ultrasound can determine whether an object is solid, contains liquid, or anywhere in between. While the ultrasound module (transducer) may encompass a separate probe, it is also within the scope of the present disclosure that the ultrasound module may be incorporated into the disclosed endocavity probe with a semiconductor detector array(s). The ultrasound and the gamma images of the target tissue and the implanted radioactive capsules may be simultaneously produced and co-registered. The target organ, e.g., prostate, is preferably continuously visualized during the course of the treatment and capsule implantation.

The method for localized radiotherapy further comprises administering to the patient one or more implantable capsules 130 of isotopes to sites of target tissue 110, e.g., cancer tissue. The seeds are typically tiny rice-sized pellets specially treated to be radioactive. The capsules of these seeds are made of a biocompatible substance such as titanium or stainless steel, and are tightly sealed to prevent leaching of the radioisotope. The capsules are sized to fit down the bore of one of the needles used in the implantation device. Since most such needles are about 18 gauge, the capsule typically has a diameter of about 0.8 mm and a length of about 4.5 mm. Each seed gives off a known amount of radioactivity into surrounding tissue. The seeds may contain any medically acceptable radioactive isotopes as long as these isotopes emit very low energy radiation, which can be mostly contained in the region of the target tissue 110. Examples of such isotopes include, but are not limited to, I-125, Ir-192, Ce-131 and Pd-103. The number of seeds implanted may range from 1 to 200 depending on the type of disease treated, the isotope selected, the volume of the diseased tissue, and the amount of radiation desired. Since each of these types of radioactive seeds gives off a known dosage of radiation, a practitioner can decide how many seeds are needed and at what dose to adequately treat a specific disease to balance the benefits of the radiotherapy with its side-effects. In contrast, the relative number of seeds is typically pre-defined for all patients, rather than customized for each individual patient or group of patients. For some applications, the seeds may be administered having different isotopes or in combination with other treatments including therapeutic agents that targets cancer cells, protein(s), analgesic(s), antibiotic(s), cardiac drug(s), neurological drug(s), anti-inflammatory agent(s), non-steroidal anti-inflammatory agent(s), and other therapeutic agents known in the art.

In a preferred embodiment, the treated disease is prostate cancer. The two radioisotopes most commonly used in prostate brachytherapy seeds are I-125 and Pd-103. Both emit low energy irradiation and have half-life characteristics ideal for treating tumors. For example, I-125 seeds decay at a rate of 50% every 60 days, so that using typical starting doses their radioactivity is almost exhausted after ten months. Pd-103 seeds decay even more quickly, losing half their energy every 17 days so that they are nearly inert after only 3 months. See, e.g., Symmetra® I-125 (Bebig GmbH, Germany); IoGold™ I-125 and IoGold™ Pd-103 (North American Scientific, Inc., Chatsworth, Calif.); Best® I-125 and Best® Pd-103 (Best Industries, Springfield, Va.); Brachyseed® I-125 (Draximage, Inc., Canada); Intersource® Pd-103 (International Brachytherapy, Belgium); Oncoseed® I-125 (Nycomed Amersham, UK); STM 1250 I-125 (Sourcetech Medical, Carol Stream, Ill.); Pharmaseed® I-125 (Syncor, Woodland Hills, Calif.); Prostaseed® I-125 (Urocor, Oklahoma City, Okla.); and I-Plant® I-125 (Implant Sciences Wakefield, Mass.). Over the ensuing several months the radiation emitted from the seeds reduces the chance of cell division and growth of the surviving cancer cells, with relatively high radiation levels causing greater death of the cancerous cells. There is an optimal amount of radiation desired in these localized regions for the purpose of treating the cancer while minimizing the adverse side effects to other normal bodily functions. For example, the inability to precisely localize the intraprostatic tumors with traditional ultrasound imaging methods and to identify the presence of diffuse cancer in the gland has led to the more common medical practice of placing many radioactive seeds throughout the gland to provide radiation treatment to the entire gland. The number of seeds may range between 50 and 100 and placed in the target tissue through a needle inserted across the perineum, i.e., skin between the rectum and the scrotum. Surgical removal of the seeds is usually not necessary because the type of radioisotope generally used decays over the several months period so that very little radiation is emitted from the seeds after this time. The analysis of the hot and cold spots using the endocavity probe is useful in brachytherapy treatments of the prostate, because it can accurately measure the radiation dose levels throughout the gland, and compare the actual radiation doses received by the patient to those desired for optimal treatment, both within and outside the suspected cancerous regions. In many cases, adjustments of the radiation dose levels can be made after the initial seed implantation depending on several factors, including the response to the brachytherapy treatment over time.

Once the capsules 130 are administered to the patient, as indicated in FIG. 3B, their precise location and activity can be readily monitored by the endocavity probe illustrated in FIGS. 1A-1B. In particular, the administered radioactive seeds will decay and emit radiation, such as gamma-ray photons with a specific energy. These photons will ionize the high-Z semiconductor detector, and generate a signal that can then be processed and mapped out on the plane parallel to the detector surface, thereby creating 1D, 2D or 3D image of the hot spot 110 within the target organ 100. By combining (co-registering) the information obtained about the location of the target tissue 110, for example, by ultrasound, with the information obtained about the location of the capsules, the practitioner can guide the precise implantation of the capsules that would avoid or cause the least amount of harm to the nearby healthy tissue. Co-registering the images can be done by an image overlay where the organ and the target tissue are rendered in one color, and the capsule(s) (seeds) are rendered in another. As illustrated in FIG. 3C, once the capsule is localized within the target tissue 110 and the needle used to administer the seeds is removed, the procedure is completed.

In an alternative embodiment, the same procedure for the localized radiotherapy can be performed without the assistance of other imaging modalities such as an ultrasound, MRI, CT, etc. For example, if radiotherapy uses one isotope ($E_1$) for the radioactive seeds (see FIG. 4B) and radiopharmaceudical tracer for imaging target tissue uses another isotope ($E_2$) (see FIG. 4A), it is possible to take images of these two isotopes in different energy windows, i.e., bin 1 for seeds and bin 2 for target tissue. By co-registering these two images (see FIG. 4C), a practitioner can target where the therapy seed should be delivered to treat the cancerous tissues. Other uses of multi-tracer imaging include the ability to simultaneously image disease with one drug and inflammation with another drug, or to image lymph nodes and blood vessels.

Figure 5A:
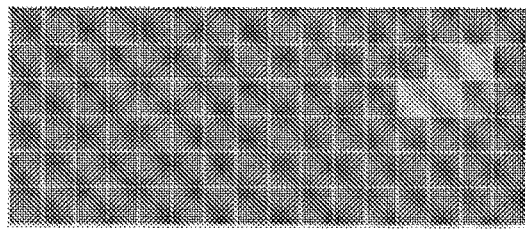
FIG. 5A illustrates a low-energy window of Am-241 acquired simultaneously with the image in FIG. 5B using "dual-energy window" approach.
Figure 5B:
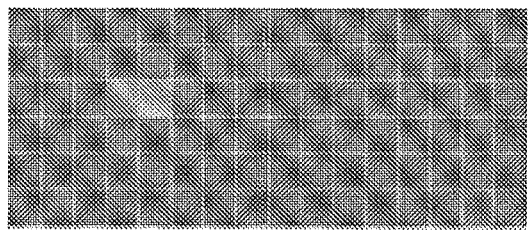
FIG. 5B illustrates a high-energy window of Co-57 acquired simultaneously with the image in FIG. 5A using "dual-energy window" approach.

FIG. 2B illustrates the signal processing electronics for the compact endocavity probe with reference to one pixel. When a gamma photon hits the active region of a pixel, it generates electron-hole pairs. The number of electron-hole pairs is proportional to the energy of the gamma photons. Under the influence of a high-voltage bias, negative charged carriers (electrons) will drift to the anode inducing a current signal on the anode. This signal 450 is collected and amplified by charge sensitive amplifier (CSA) in an ASIC 600 or other equivalent processing unit. The output signal from the CSA is compared with a preset threshold. If the signal is larger than the threshold, a trigger signal is generated, causing the counter of that channel to increase by one. Depending on the applications, there can be several different thresholds, allowing the user to detect photons with different energies and produce images for each separate energy bin. Correspondingly, there are multiple energy bins (e.g., 5 bins are illustrated in FIG. 2B) to count photons with different energies. The readout control logic reads out the values of all the energy bins of all the pixels and sends them to the computer 700 for imaging reconstruction and display. Thus, multiple energy windows (bins) of the probe can be used by administering a radiotracer with an isotope that differs from the isotope used in the seed. Because different isotopes generate different gamma-ray energy signals, the disclosed endocavity probe can generate separate energy bins. In one exemplary embodiment, a dual energy window approach is used in the radiotherapy with Am-241 and Co-57 isotopes. The signal from both isotopes is acquired simultaneously. As illustrated in FIGS. 5A and 5B, Am-241 is imaged in a low-energy window, whereas Co-57 is imaged in a high-energy window. Alternatively, instead of generating separate windows or bins, the same procedure can be performed using one window, as long as the energy window is wide enough to cover the energy signals (lines) from both radioactive seeds and the tracer.

Figure 6:
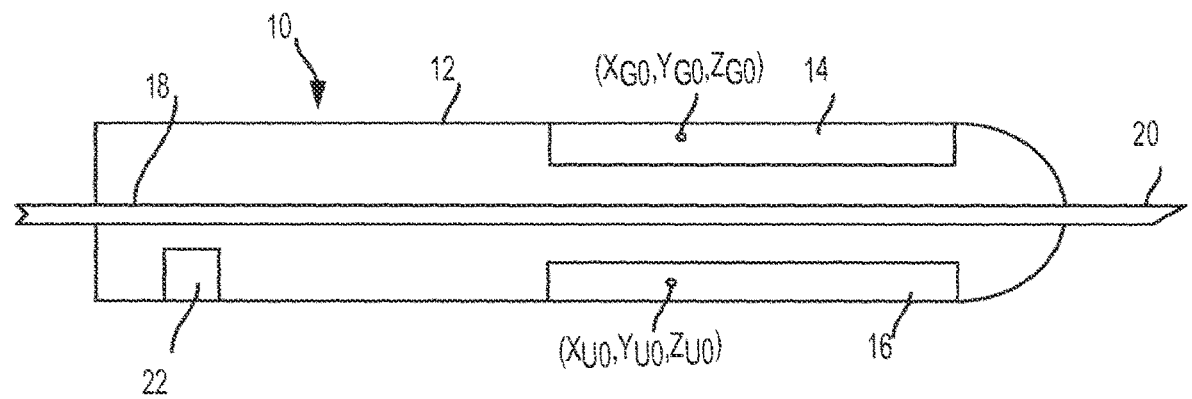
FIG. 6 is a schematic drawing of an exemplary dual-modality endocavity diagnostic probe with a needle extending therethrough.
Figure 7:
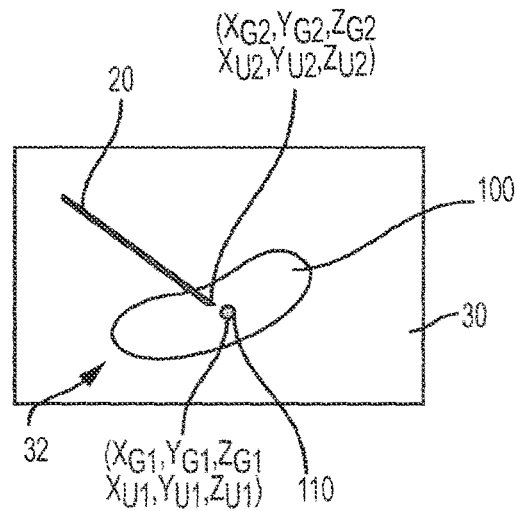
FIG. 7 is a schematic drawing showing a multi-modality imaging using the endocavity diagnostic probe of FIG. 6.

With reference to FIGS. 6 and 7, a dual-modality endocavity probe 10 in accordance with an exemplary embodiment of the invention will be described. The probe 10 includes a housing 12 which houses a nuclear detector system 14 and an ultrasound detector system 16. The housing 12 may be made of a material that allows radiation/waves to pass through or it may include appropriate windows or the like for the passage of the radiation and/or waves. The nuclear detector system 14 may be any of the systems described herein or a similar system configured to generate an image in response to radioactive tracers or the like. The nuclear detector system 14 defines a first three-dimensional coordinate system with the nuclear detector defining an origin ($X_{G0}$, $Y_{G0}$, $Z_{G0}$) thereof. The ultrasound detector system 16 components are compact components integrated within the housing 12 of the probe 10 and configured to generate high frequency sound waves and generate an image based on the echo which is received back by the sensor. Similarly, the ultrasound detector system 16 defines a second three-dimensional coordinate system with the ultrasound detector defining an origin ($X_{U0}$, $Y_{U0}$, $Z_{U0}$) thereof.

The probe housing 12 is further configured to guide the positioning of a needle 20 or other medical instrument. In the present embodiment, the housing 12 includes a through passage 18 through which the needle 20 may be passed, however, the housing may have other configurations which facilitate guidance of the needle 20. The needle 20 is preferably a dual purpose needle, capable of extracting targeted biopsy tissue as well as delivering treatment medication to a target area.

The system further includes a data processing module 22 which may positioned within the housing 12 or may be external thereto and otherwise communicate with the systems 14 and 16. The data processing module 22 is configured to process data detected by the nuclear detector system 14 and the ultrasound detector system 16 and generate an image 32 based on the data detected by each system and display the image 32 on a monitor 30 or the like. In this regard, each system 14, 16 identifies independent locations of the various points of an object within the respective coordinate system. For example, as illustrated in FIG. 7, the hot spot 110 may have a point located within the nuclear detector system 14 at ($X_{G1}$, $Y_{G1}$, $Z_{G1}$) while the same point is located at ($X_{U1}$, $Y_{U1}$, $Z_{U1}$) of the ultrasound detector system 16. The data processing module 22 is configured to co-register these two distinct coordinate systems by utilizing a coordinate transformation that mathematically overlays the coordinate systems of the two imagers. With the co-registered information, an accurate image 32 may be produced.

A user interface may be associated with the monitor 30 for managing the acquisition of imaging data and managing the targeted biopsy and treatment procedures. The data processing module 22 can be configured to combine the data and create a single image therefrom or may create separate images from the data from each system 14, 16 and then co-register the images, through coordinate transformation, to form the output image 32.

As illustrated in FIG. 7, the needle 20 will be imaged relative to the hot spot 110 of the imaged organ 100. The needle 20, due to its different properties from its surrounding, can be imaged by the ultrasound system 16 of the probe 10 during a biopsy procedure. The needle 20 may additionally or alternatively have a radiation signature so it can also be imaged by the nuclear detector system 14. During a treatment procedure, the needle 20 may be imaged by both the radiation system 14 and/or the ultrasound system 16 since the needle and/or treatment medication will also have a radiation signature as explained above. As such, the needle 20 may have a point which is identified on both systems as ($X_{G2}$, $Y_{G2}$, $Z_{G2}$) and ($X_{U2}$, $Y_{U2}$, $Z_{U2}$). Again, the data processing module utilizes coordinate transformation to co-register the two coordinate systems.

The tip of the needle 20 may be moved to the hot spot 110, to perform either a biopsy or treatment, by hand, e.g. a surgeon viewing the image 32 and manipulating the probe 10 and/or needle 20 based thereon. Alternatively, the needle 20 may be moved to the hot spot 110 via an automated procedure, e.g. a robot controlling the position of the probe 10 and/or needle 20, based on the detected relative position of the tip of the needle 20 and the hot spot 110.

All publications and patents mentioned in the above specification are herein incorporated by reference. Various modifications and variations of the described probe and its components will be apparent to those skilled in the art without departing from the scope and spirit of the invention. Although the disclosure has been described in connection with specific preferred embodiments, it should be understood that the invention as claimed should not be unduly limited to such specific embodiments. Indeed, those skilled in the art will recognize, or be able to ascertain using no more than routine experimentation, many equivalents to the specific embodiments of the invention described herein. Such equivalents are intended to be encompassed by the following claims.

The invention claimed is:

1. A dual modality endocavity imaging system, comprising:

a housing configured to maintain a relative position of detector systems housed within the housing with respect to the housing and objects being imaged;

a nuclear detector system housed within the housing, the nuclear detector system defining a single fixed first origin of a first three-dimensional coordinate system and configured for detecting nuclear radiation imaging data by guiding photons, using a collimator with interleaved apertures, toward a detector to generate a signal to be processed and mapped out on a plane parallel to a surface of the detector facing the collimator as single fixed three-dimensional coordinate positions relative to the single fixed first origin from which a distance between the fixed first origin and a position of an endocavity object of interest, relative to the fixed first origin, is calculated;

an ultrasound detector system housed within the housing, the ultrasound detector system defining a single fixed second origin of a single fixed second three-dimensional coordinate system and configured for detecting ultrasound imaging data as single fixed three-dimensional coordinate positions relative to the single fixed second origin;

a treatment delivery needle supported by the housing and adjustably positionable relative thereto, the treatment delivery needle having a radiation signature detectable by the nuclear detector system; and a data processing module configured to receive the nuclear radiation imaging data from the nuclear detector system which includes first three-dimensional coordinate system data on the position of the endocavity object of interest and a position of the treatment delivery needle relative to the fixed first origin, and the ultrasound imaging data which includes second three-dimensional coordinate system data on the position of the treatment delivery needle; wherein the data processing module is further configured to combine the nuclear radiation imaging data with the ultrasound imaging data utilizing coordinate transformation to co-register points of the first and second three-dimensional coordinate systems based on at least a point of the treatment delivery needle which is identified in the nuclear radiation imaging data and the ultrasound imaging data;

the data processing module further configured to calculate a distance between the treatment delivery needle and the endocavity object of interest; and wherein the data processing module is further configured to generate and output an image showing the relative distance between the treatment delivery needle and the endocavity object of interest.

2. The dual modality endocavity imaging system as recited in claim 1, wherein the data processing module is configured to generate separate images from the detected ultrasound and nuclear radiation data and to utilize coordinate transformation on the separate images to co-register the images.

3. The dual modality endocavity imaging system as recited in claim 1, wherein the data processing module is configured to utilize coordinate transformation to co-register the detected ultrasound and nuclear radiation data and thereafter generate the output image.

4. The dual modality endocavity imaging system as recited in claim 1, wherein the data processing module is further configured to output information indicating a relative position of the treatment delivery needle relative to the endocavity object of interest.

5. The dual modality endocavity imaging system as recited in claim 1, wherein the system further includes a monitor and the output image is displayed on the monitor.

6. A method of imaging an object of interest within an endocavity, comprising the steps of:
    inserting a portion of a housing of a dual modality endocavity imaging system into the endocavity, the system including a treatment delivery needle having a radiation signature detectable by a nuclear detector system and which is supported by and moveable relative to the housing and a collimator with interleaved apertures;
    fixing a single physical position of the housing within the endocavity so that the single relative position of the housing and the object being imaged is stationary and fixed, the housing configured to maintain a relative position of detector systems housed within the housing with respect to the housing;
    activating the nuclear detector system housed within the housing, the nuclear detector system defining a single fixed first origin of a first three-dimensional coordinate system, and detecting nuclear radiation imaging data by guiding photons, using the collimator with the interleaved apertures, toward a detector to generate a signal to be processed and mapped out on a plane parallel to a surface of the detector facing the collimator as single fixed three-dimensional coordinate positions relative to the single fixed first origin from which a distance between the fixed first origin and a position of the object of interest, relative to the fixed first origin, is calculated;
    activating an ultrasound detector system and detecting ultrasound imaging data representing objects, including the object of interest and the treatment delivery needle, within the endocavity, including second three-dimensional coordinate system data of the objects relative to a single fixed second origin defined at the ultrasound detector system;
    receiving, at a data processing module, nuclear radiation imaging data which includes first three-dimensional coordinate system data on the position of the object of interest and a position of the treatment delivery needle relative to the fixed first origin, and the ultrasound imaging data which includes second three-dimensional coordinate system data on the position of the treatment delivery needle;
    utilizing coordinate transformation to co-register the first three-dimensional coordinate system data and the second three-dimensional coordinate system data based on at least a point of the treatment delivery needle which is identified in the nuclear radiation imaging data and the ultrasound imaging data;
    to calculating a distance between the treatment delivery needle and the object of interest; and
    generating and outputting an image showing the distance between the treatment delivery needle and the object of interest.

7. The method as recited in claim 6, further comprising positioning of the treatment delivery needle relative to the object of interest based on the output image.

8. The method as recited in claim 7, wherein the step of positioning of the treatment delivery needle includes moving the treatment delivery needle relative to the housing.

9. The method as recited in claim 7, wherein the step of positioning of the treatment delivery needle is performed via an automated process.

10. The method as recited in claim 6, further comprising performing a biopsy with the treatment delivery needle.

11. The method as recited in claim 6, further comprising delivering a treatment medicine.

12. The method as recited in claim 6, wherein the step of generating the image includes generating separate images from the detected first and second three-dimensional coordinate system data and co-registering the separate images to generate the output image.

* * * * *